US011561938B1

(12) United States Patent
Sutariya et al.

(10) Patent No.: US 11,561,938 B1
(45) Date of Patent: Jan. 24, 2023

(54) CLOSED-LOOP INTELLIGENCE

(71) Applicant: CERNER INNOVATION, INC., Kansas City, KS (US)

(72) Inventors: Bharat B. Sutariya, Parkville, MO (US); Ryan Alan Brush, Overland Park, KS (US); Cole Anthony Erdmann, Kansas City, MO (US)

(73) Assignee: CERNER INNOVATION, INC., North Kansas City, MO (US)

( * ) Notice: Subject to any disclaimer, the term of this patent is extended or adjusted under 35 U.S.C. 154(b) by 519 days.

(21) Appl. No.: 16/528,194

(22) Filed: Jul. 31, 2019

Related U.S. Application Data

(60) Provisional application No. 62/712,581, filed on Jul. 31, 2018.

(51) Int. Cl.
*G06F 16/21* (2019.01)
*G16H 10/60* (2018.01)
*G06N 20/00* (2019.01)

(52) U.S. Cl.
CPC ............. *G06F 16/21* (2019.01); *G06N 20/00* (2019.01); *G16H 10/60* (2018.01)

(58) Field of Classification Search
CPC .......... G06F 16/21; G06N 20/00; G16H 10/60
See application file for complete search history.

(56) References Cited

U.S. PATENT DOCUMENTS

| | | | |
|---|---|---|---|
| 2016/0034809 A1* | 2/2016 | Trenholm | G06K 9/00536 706/20 |
| 2016/0358099 A1* | 12/2016 | Sturlaugson | G06N 5/043 |
| 2019/0034591 A1* | 1/2019 | Mossin | G06N 3/08 |
| 2019/0340095 A1* | 11/2019 | Faibish | G06F 11/302 |

\* cited by examiner

*Primary Examiner* — Pei Yong Weng
(74) *Attorney, Agent, or Firm* — Shook, Hardy & Bacon L.L.P.

(57) ABSTRACT

Methods, computer systems, and computer-storage medium are provided for providing closed-loop intelligence. A selection of data is received, at a cloud service, from a database comprising data from a plurality of sources in a Fast Healthcare Interoperability Resources (FHIR) format to build a data model. After a feature vector corresponding to the data model is extracted, a selection of an algorithm for a machine learning model to apply to the data model is received. A portion of the selection of data is utilized for training data and test data and the machine learning model is applied to the training data. Once the model is trained, the trained machine learning model can be saved at the cloud service, where it may be accessed by others.

20 Claims, 5 Drawing Sheets

CLOSED-LOOP INTELLIGENCE

CROSS-REFERENCE TO RELATED APPLICATIONS AND PRIORITY CLAIM

This application claims the benefit of U.S. Provisional Patent Application No. 62/712,581, filed Jul. 31, 2018, entitled "Closed-Loop Intelligence,", the entire contents of which is incorporated herein by reference.

BACKGROUND

The advent of powerful servers, large-scale data storage and other information infrastructure has spurred the development of advanced data warehousing and data mining applications. Structured query language (SQL) engines, on-line analytical processing (OLAP) databases and inexpensive large disk arrays have for instance been harnessed in financial, scientific, medical, and other fields to capture and analyze vast streams of transactional, experimental, and other data. The mining of that data can reveal sales trends, weather patterns, disease epidemiology and other patterns not evident from more limited or smaller-scale analysis.

In the case of medical data management, the task of receiving, conditioning, and analyzing large quantities of clinical information is particularly challenging. The sources of medical data for an organization, for instance, may include various hospitals, laboratories, research or other facilities, each of which may generate data records at different times and in widely varying formats. Those various data records may be presorted or pre-processed to include different relationships between different fields of that data, based upon different assumptions or database requirements. When received in a large-scale data warehouse, the aggregation of all such differing data points may be difficult to store in a physically or logically consistent structure. Data records may, for instance, contain different numbers or types of fields, which may have to be conformed to a standard format for warehousing and searching.

Even when conditioned and stored, that aggregation of data may prove difficult to analyze or mine for the most clinically relevant or other data, such as those indicating a disease outbreak or adverse reactions to drugs or other treatments. Clinical systems are often extremely large, with a high volume of data, and utilizing that data is inefficient and requires significant processing overhead. This heavy back-end processing is time-consuming and particularly burdensome to the server and network infrastructure. Moreover, organizations are forced to rely on internally created predictive models that are tailored to internal data. Consequently, these predictive models are trained and tested on internal data only and do not benefit from training and testing on an entire population of data. As a result these predictive models are not usable or accessible by other organizations. Accordingly, currently there is not an efficient and convenient system and/or method that enables structured views of data to be aggregated into a big data architecture, to train and test predictive tools on an entire population of data, push insights gained from the predictive tools on the entire population of data into a clinical workflow, and provide access and use to these predictive tools by other organizations.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for providing closed-loop intelligence. To do so, a selection of data is received, at a cloud service, from a database comprising data from a plurality of sources in a Fast Healthcare Interoperability Resources (FHIR) format to build a data model. (FHIR is a standard describing data formats and elements (known as "resources") and an Application Programming Interface (API) for exchanging electronic healthcare records. FHIR is known to those having ordinary skill in the art and, accordingly, is not further described herein.) After a feature vector corresponding to the data model is extracted, a selection of an algorithm for a machine learning model to apply to the data model is received. A portion of the selection of data is utilized for training data and test data and the machine learning model is applied to the training data. Once the model is trained, the trained machine learning model can be saved at the cloud service, where it may be accessed by others.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As noted in the Background, the advent of powerful servers, large-scale data storage and other information infrastructure has spurred the development of advanced data warehousing and data mining applications. Structured query language (SQL) engines, on-line analytical processing (OLAP) databases and inexpensive large disk arrays have for instance been harnessed in financial, scientific, medical, and other fields to capture and analyze vast streams of transactional, experimental, and other data. The mining of that data can reveal sales trends, weather patterns, disease epidemiology and other patterns not evident from more limited or smaller-scale analysis.

In the case of medical data management, the task of receiving, conditioning, and analyzing large quantities of clinical information is particularly challenging. The sources of medical data for an organization, for instance, may include various hospitals, laboratories, research or other facilities, each of which may generate data records at different times and in widely varying formats. Those various data records may be presorted or pre-processed to include different relationships between different fields of that data, based upon different assumptions or database requirements. When received in a large-scale data warehouse, the aggregation of all such differing data points may be difficult to store in a physically or logically consistent structure. Data records may, for instance, contain different numbers or types of fields, which may have to be conformed to a standard format for warehousing and searching.

Even when conditioned and stored, that aggregation of data may prove difficult to analyze or mine for the most clinically relevant or other data, such as those indicating a disease outbreak or adverse reactions to drugs or other treatments. Clinical systems are often extremely large, with a high volume of data, and utilizing that data is inefficient and requires significant processing overhead. This heavy back-end processing is time-consuming and particularly burdensome to the server and network infrastructure. Moreover, organizations are forced to rely on internally created predictive models that are tailored to internal data. Consequently, these predictive models are trained and tested on internal data only and do not benefit from training and testing on an entire population of data. As a result these predictive models are not usable or accessible by other organizations. Accordingly, currently there is not an efficient and convenient system and/or method that enables structured views of data to be aggregated into a big data architecture, to train and test predictive tools on an entire population of data, push insights gained from the predictive tools on the entire population of data into a clinical workflow, and provide access and use to these predictive tools by other organizations.

Embodiments of the present invention can empower an organization's ability to harness and utilize pertinent data. Embodiments present advantages over other systems which are limited to predictive models that are tailored to internal data, trained and tested on internal data only, and not usable or accessible by other organizations.

Generally, closed-loop intelligence enables an organization to create ad-hoc data sets, train and test predictive models on an entire population of data, and push insights gained into a clinical workflow. Moreover, once a trained model is available at a cloud service, the trained model may be accessible by other organizations. Initially, a selection of data is received, at the cloud service, from a database comprising data from a plurality of sources in a Fast Healthcare Interoperability Resources (FHIR) format to build a data model. Although the data is described herein as being in a FHIR format, it is contemplated that the data may be in any format used by clinical systems. After a feature vector corresponding to the data model is extracted, a selection of an algorithm for a machine learning model to apply to the data model is received. A portion of the selection of data is utilized for training data and test data and the machine learning model is applied to the training data. Once the model is trained, the trained machine learning model can be saved at the cloud service, where it may be accessed by others.

Additionally, resources of the cloud service required by an organization for a particular study may also be conserved (e.g., memory, number of processors utilized, processing time) because the organizations may scale the data being used to train and test the models to need (e.g., a particular cohort being studied) and utilize models and/or data sets created by others. Moreover, an organization may utilize the output of the trained models to further streamline workflows within the organization. The streamlined workflows may result in additional data points that can be utilized by an organization accessing the cloud service. For example, the additional data points can be utilized for training and/or testing the models or supplementing a data set.

Accordingly, one embodiment of the present disclosure is directed to one or more non-transitory computer-storage media storing computer-usable instructions that, when used by one or more processors, cause the one or more processors to perform operations to provide closed-loop intelligence. The operations comprise receiving a selection of data, at a cloud service, from a database comprising data from a plurality of sources in a Fast Healthcare Interoperability Resources (FHIR) format to build a data model. The operations also comprise extracting a feature vector corresponding to the data model. The operations further comprises receiving a selection of an algorithm for a machine learning model to apply to the data model. The operations also comprise utilizing a portion of the selection of data for training data and test data. The operations further comprise applying the machine learning model to the training data.

In another embodiment, the present disclosure directed to a computerized method for providing closed-loop intelligence. The method comprises receiving a selection of data, at a cloud service, from a database comprising data from a plurality of sources. The computerized method also comprises utilizing a Fast Healthcare Interoperability Resources (FHIR) format to build a data model. The method further comprises projecting conditions selected by a user onto the data model.

In yet another embodiment, the present disclosure is directed to a system in a healthcare computing environment for providing closed-loop intelligence. The system comprises a processor; and a non-transitory computer storage medium storing computer-useable instructions that, when used by the processor, cause the processor to: receive a selection of an algorithm for a machine learning model to apply to the data model; utilizing a portion of the selection of data for training data and test data; and apply the machine learning model to the training data.

Figure 1:
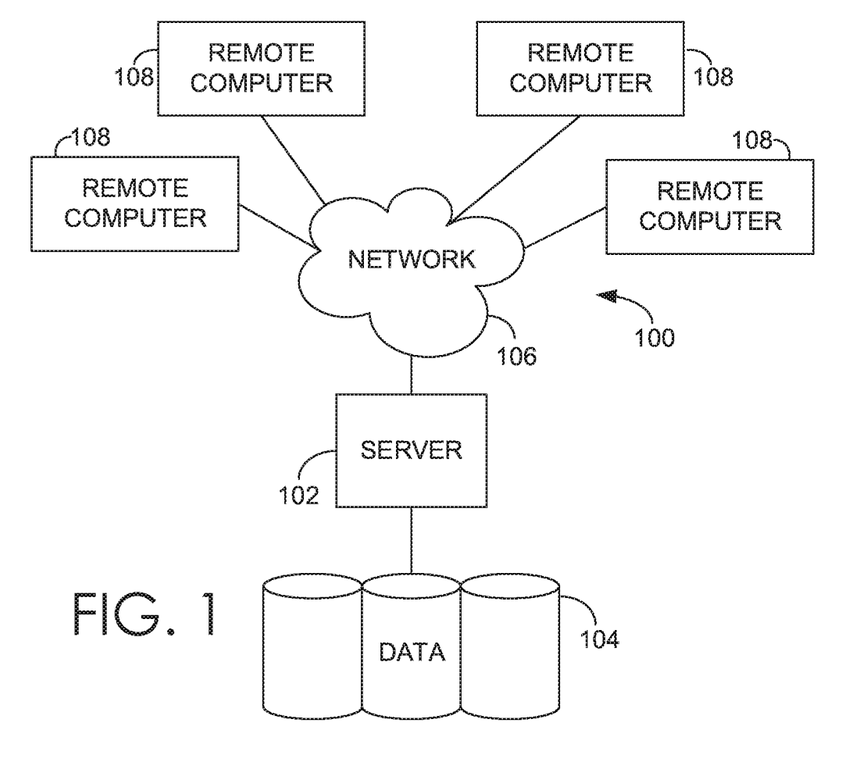
FIG. 1 is a block diagram of an exemplary computing environment suitable to implement embodiments of the present invention.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs), wide area networks (WANs), and/or wireless LANs (WLANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
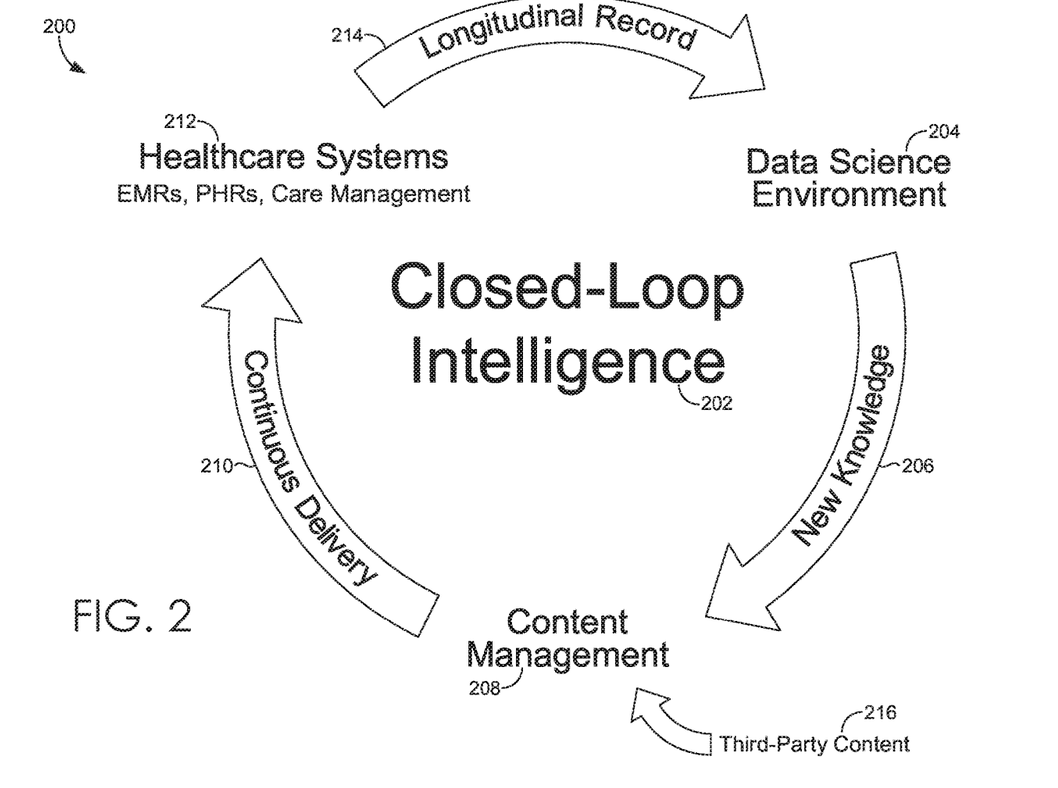
FIG. 2 is a circular flow diagram of an exemplary data flow path suitable to implement embodiments of the present invention.

FIG. 2 illustrates an exemplary circular flow diagram 200. As illustrated in the flow diagram 200, closed-loop intelligence system 202 is an elastic cloud that enables resources of the system to be provisioned and de-provisioned as needed. FHIR-based views of a longitudinal record 214 enable all authorized data to be accessed in a secure environment (e.g., data science environment 204) with various tools to analyze the data.

For clarity, the longitudinal record 214 corresponds to a comprehensive clinical summary of a patient-based clinical experience and might come from a variety of sources and/or exist in a variety of formats including for example, narratives and discretized data. Examples of sources can include patient data from different data sources, such as different medical entities, traditional hospitals, walk-in clinics, urgent care facilities, other locations that render medical services, as well as in-home patient monitors and patient-wearable sensors or monitors (collectively, "healthcare systems" 212).

In one embodiment, the longitudinal record 214 includes one or more of patient data, patient records, previously determined analysis or disposition, which are associated with the patient, recommended treatments, previously determined patient conditions, and past actions performed for the patient. In some embodiments, patient data can include lab results, real time or near real time information such as data provided by a physician, including information based on observation or a patient's explanation, information provided by a sensor (for example, blood pressure or heart rate), or other patient data. In some embodiments, patient records can include electronic medical records ("EMR"), health information exchange ("HIE"), personal health record ("PHR"), patient claims, and other health records associated with a patient.

Ad-hoc data sets can be created from the longitudinal record 214 for analysis in data science environment 204. This enables a user to take a very complex data set and turn it into much simpler tables that provides greater efficiencies and reduces costs associated with using the closed-loop intelligence system 202. Moreover, closed-loop intelligence system 202 enables self-service cohort discovery and exploratory analysis. This helps create new knowledge 206 that can be fed back into the closed-loop intelligence system 202 via insights gained from various models and algorithms that may be provided in the data science environment 204.

In some embodiments, a content management 208 service enables new knowledge 206 and other data corresponding to the closed-loop intelligence system 202, including third-party content 216, to be stored in a FHIR format in the closed-loop intelligence system 202. As can be appreciated, all content, including algorithms and models created or provided in the data science environment 204, and stored in the closed-loop intelligence system 202 may be accessed or utilized by any user provided the user has the appropriate access and credentials.

Figure 3:
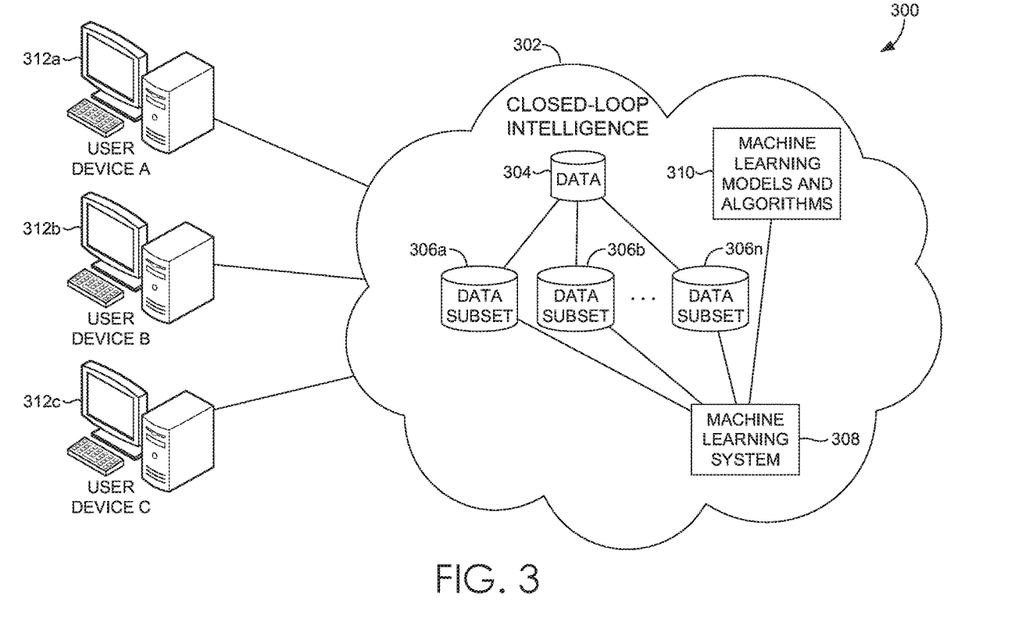
FIG. 3 is a block diagram of an exemplary system for providing closed-loop intelligence suitable to implement embodiments of the present invention.

Turning now to FIG. 3, an exemplary computing system environment 300 is depicted suitable for use in implementing embodiments of the present invention. The computing system environment 300 is merely an example of one suitable computing system environment and is not intended to suggest any limitation as to the scope of use or functionality of embodiments of the present invention. Neither should the computing system environment 300 be interpreted as having any dependency or requirement related to any single module/component or combination of modules/components illustrated therein.

The computing system environment 300 includes user devices 312*a*, 312*b*, 312*c*, and a closed-loop intelligence system 302 (provided as an elastic cloud service), all in communication with one another via a network. The closed-loop intelligence system 302 includes data store 304, data subsets 306*a*-306*n*, machine learning system 308, and machine learning models and algorithms 310.

As mentioned, the components of the computing system environment 300 may communicate with each other via a network, which may include, without limitation, one or more local area networks (LANs) and/or wide area networks (WANs). Such networking environments are commonplace in offices, enterprise-wide computer networks, intranets, and the Internet.

In some embodiments, one or more of the illustrated components/modules may be implemented as stand-alone applications. In other embodiments, one or more of the illustrated components/modules may be integrated directly into the operating system of the user devices 312*a*, 312*b*, 312*c* or provided via a network. The components/modules illustrated in FIG. 3 are exemplary in nature and in number and should not be construed as limiting. Any number of components/modules may be employed to achieve the desired functionality within the scope of embodiments hereof. Further, components/modules may be located on any number of servers. By way of example only, the closed-loop intelligence system 302 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 304 is configured to store information for use by, for example, the user devices 312*a*, 312*b*, 312*c* or the closed-loop intelligence system 302 (e.g., the machine learning system 308 and/or the machine learning models and algorithms 310). The information stored in association with the data store 304 is configured to be searchable for one or more items of information stored in association therewith. The information stored in association with the data store 304 may comprise general information used by the closed-loop intelligence system 302 and/or the user devices 312*a*, 312*b*, 312*c*. The information stored in association with the data store may be received from other systems (e.g., healthcare systems), which may include any number or type of medical devices that may be utilized to provide or measure patient care to a patient.

In embodiments, the data store 304 may store electronic health records (EHRs) of patients associated with one or more healthcare facilities. EHRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. In some embodiments, the data store 304 may include data received from health information exchanges ("HIEs"), personal health records ("PHRs"), patient claims, and other health records associated with a patient.

The data store 304 may store FHIR-based views of a longitudinal record that enables all authorized data to be accessed in a secure environment with various tools to analyze the data. As mentioned, the longitudinal record corresponds to a comprehensive clinical summary of a patient-based clinical experience and might come from a variety of sources and/or exist in a variety of formats including for example, narratives and discretized data. Examples of sources can include patient data from different data sources, such as different medical entities, traditional hospitals, walk-in clinics, urgent care facilities, other locations that render medical services, as well as in-home patient monitors and patient-wearable sensors or monitors.

In some embodiments, ad-hoc data subsets 306a, 306b, 306c can be created by selecting data from data store 302 for analysis. This enables a user to take a very complex data set and turn it into much simpler tables that provides greater efficiencies and reduces costs associated with using the closed-loop intelligence system 302. In this way, the closed-loop intelligence system 302 enables self-service cohort discovery and exploratory analysis. As mentioned, this helps create new knowledge that can be fed back into the closed-loop intelligence system 302 via insights gained from various models and algorithms 310 that may be created or provided in the data science environment (e.g., data science environment 204 of FIG. 2).

In some embodiments, a content management service (such as the content management service 208 of FIG. 2) enables knowledge (i.e., the insights gained from various models and algorithms) and other data corresponding to the closed-loop intelligence system 302, including third-party content, to be stored in a FHIR format in the closed-loop intelligence system 302. As can be appreciated, all content, including models and algorithms 310, data 302, and data subsets 306a, 306b, 306c, may be accessed or utilized by any user provided the user has the appropriate access and credentials.

The content and volume of such information in the data store 302 are not intended to limit the scope of embodiments of the present invention in any way. Further, though illustrated as a single, independent component, the data store 302 may, in fact, be a plurality of storage devices, for instance, a database cluster, portions of which may reside in the closed-loop intelligence system 302 (provided as an elastic cloud service).

In practice, a selection of data may be received from user device(s) 312a, 312b, 312c, at a cloud service (e.g. closed-loop intelligence system 302), from a database (e.g., data store 302) comprising data from a plurality of sources in a Fast Healthcare Interoperability Resources (FHIR) format to build a data model. A feature vector corresponding to the data model may be extracted. For example, a user may desire to select as inputs average glucose level, average creatinine, and chest pain.

After selecting an algorithm (such as from machine learning models and algorithms 310) to build the machine learning pipeline, to apply to the data model, a portion of the selection of data can be utilized for training data and for test data. In various embodiments, the algorithms may include one or more of: logistic regression, linear regression, decision tree classifier, decision tree regression, random forest classifier, random forest regression, gradient-boosted tree classifier, gradient-boosted tree regression, multilayer perceptron classifier survival regression, support vector machine, isotonic regression, one-vs-rest classifier, linear methods, naïve Bayes, tree ensembles, Spark natural language processing (NLP), random forests, gradient-boosted trees (GTSs), or custom libraries. After the machine learning model is applied to the training data (at the machine learning system 308), the machine learning model is trained and can be saved at the cloud service (e.g. at the machine learning models and algorithms 310 of the closed-loop intelligence system 302).

In embodiments, content for the data model is received automatically from a plurality of healthcare systems. As mentioned, the plurality of healthcare systems may comprise electronic medical records, personal health records, care management systems, or third party content. This data may be communicated to data store 304 by the plurality of healthcare systems where it is assembled into FHIR views and accessible to be selected by a user via user device(s) 312a, 312b, 312c. Assembling the content into FHIR views may comprise cleaning and normalizing the content. As can be appreciated, the content is then enabled for utilization in analytics and machine learning at the closed-loop intelligence system.

The user device(s) 312a, 312b, 312c may be any type of computing device(s) used within a healthcare facility to receive, display, and send information to a user, such as a clinician. The user device(s) 312a, 312b, 312c may be capable of communicating via a network with closed-loop intelligence system 302. Such devices may include any type of mobile and portable devices including cellular telephones, personal digital assistants, tablet PCs, smart phones, and the like.

As shown, the user device(s) 312a, 312b, 312c include a display screen. The display screen is configured to display information to the user of the user device(s) 312a, 312b, 312c. The information may include communications initiated by and/or received by the user device(s) 312a, 312b, 312c and/or closed-loop intelligence system 302. Embodiments are not intended to be limited to visual display but rather may also include audio presentation, combined audio/visual presentation, haptic feedback, and the like.

Components of the user device(s) 312a, 312b, 312c may include a processing unit, internal system memory, and a suitable system bus for coupling various system components, including one or more data stores for storing information (e.g., files and metadata associated therewith). The user device(s) 312a, 312b, 312c typically include, or have access to, a variety of computer-readable media.

The closed-loop intelligence service 302 may utilize one or more machine learning algorithms 310. For example, a generic decision tree is a decision support tool that arrives at a decision after following steps or rules along a tree-like path. While most decision trees are only concerned about the final destination along the decision path, alternating decision trees take into account every decision made along the path and may assign a score for every decision encountered. Once the decision path ends, the algorithm sum all of the incurred scores to determine a final classification. In some embodiments, the alternating decision tree algorithm may be further customized. For example, the alternating decision tree algorithm may be modified by wrapping it in other algorithms.

A machine learning algorithm may use a generic cost matrix. The intuition behind the cost matrix is as follows. If the model predicts a member to be classified in group A, and the member really should be in group A, no penalty is assigned. However, if this same member is predicted to be in group B, C, or D, a 1-point penalty will be assigned to the model for this misclassification, regardless of which group the member was predicted to be in. Thus, all misclassifications are penalized equally. However, by adjusting the cost matrix, penalties for specific misclassifications can be assigned. For example, where someone who was truly in group D was classified in group A, the model could increase the penalty in that section of the cost matrix. A cost matrix such as this may be adjusted as needed to help fine tune the model for different iterations, and may be based on the specific patient in some embodiments.

With regards to a multi-class classifier, some machine learning algorithms, such as alternating decision trees, generally only allow for the classification into two categories (e.g. a binary classification). In cases where it is desired to classify three or more categories, a multi-class classifier is used.

In order to assist the alternating decision tree in selecting best features for predictive modeling, an ensemble method called rotation forest may be used. The rotation forest algorithm randomly splits the dataset into a specified number of subsets and uses a clustering method called Principal Component Analysis to group features deemed useful. Each tree is then gathered (i.e., "bundled into a forest") and evaluated to determine the features to be used by the base classifier.

Various alternative classifiers may be used to provide the closed-loop intelligence. Indeed, there are thousands of machine learning algorithms, which could be used in place of, or in conjunction with, the alternating decision tree algorithm. For example, one set of alternative classifiers comprise ensemble methods.

Ensemble methods use multiple, and usually random, variations of learning algorithms to strengthen classification performance. Two of the most common ensemble methods are bagging and boosting. Bagging methods, short for "bootstrap aggregating" methods, develop multiple models from random subsets of features from the data ("bootstrapping"), assigns equal weight to each feature, and selects the best-performing attributes for the base classifier using the aggregated results. Boosting, on the other hand, learns from the data by incrementally building a model, thereby attempting to correct misclassifications from previous boosting iterations.

Regression models are frequently used to evaluate the relationship between different features in supervised learning, especially when trying to predict a value rather than a classification. However, regression methods are also used with other methods to develop regression trees. Some algorithms combine both classification and regression methods; algorithms that used both methods are often referred to as CART (Classification and Regression Trees) algorithms.

Bayesian statistical methods are used when the probability of some events happening are, in part, conditional to other circumstances occurring. When the exact probability of such events is not known, maximum likelihood methods are used to estimate the probability distributions. A textbook example of Bayesian learning is using weather conditions, and whether a sprinkler system has recently gone off, to determine whether a lawn will be wet. However, whether a homeowner will turn on their sprinkler system is influenced, in part, to the weather. Bayesian learning methods, then, build predictive models based on calculated prior probability distributions.

Another type of classifiers comprise artificial neural networks. While typical machine learning algorithms have a pre-determined starting node and organized decision paths, the structure of artificial neural networks are less structured. These algorithms of interconnected nodes are inspired by the neural paths of the brain. In particular, neural network methods are very effective in solving difficult machine learning tasks. Much of the computation occurs in "hidden" layers.

By way of example and not limitation, other classifiers and methods that may be utilized include (1) decision tree classifiers, such as: C4.5—a decision tree that first selects features by evaluating how relevant each attribute is, then using these attributes in the decision path development; Decision Stump—a decision tree that classifies two categories based on a single feature (think of a single swing of an axe); by itself, the decision stump is not very useful, but becomes more so paired with ensemble methods; LADTree—a multi-class alternating decision tree using a LogitBoost ensemble method; Logistic Model Tree (LMT) —a decision tree with logistic regression functions at the leaves; Naive Bayes Tree (NBTree) —a decision tree with naive Bayes classifiers at the leaves; Random Tree—a decision tree that considers a pre-determined number of randomly chosen attributes at each node of the decision tree; Random Forest—an ensemble of Random Trees; and Reduced-Error Pruning Tree (REPTree) —a fast decision tree learning that builds trees based on information gain, then prunes the tree using reduce-error pruning methods; (2) ensemble methods such as: AdaBoostM1—an adaptive boosting method; Bagging—develops models using bootstrapped random samples, then aggregates the results and votes for the most meaningful features to use in the base classifier; LogitBoost—a boosting method that uses additive logistic regression to develop the ensemble; MultiBoostAB—an advancement of the AdaBoost method; and Stacking—a method similar to boosting for evaluating several models at the same time; (3) regression methods, such as Logistic Regression—regression method for predicting classification; (4) Bayesian networks, such as BayesNet—Bayesian classification; and NaiveBayes—Bayesian classification with strong independence assumptions; and (4) artificial neural networks such as MultiLayerPerception—a forward-based artificial neural network.

Figure 4:
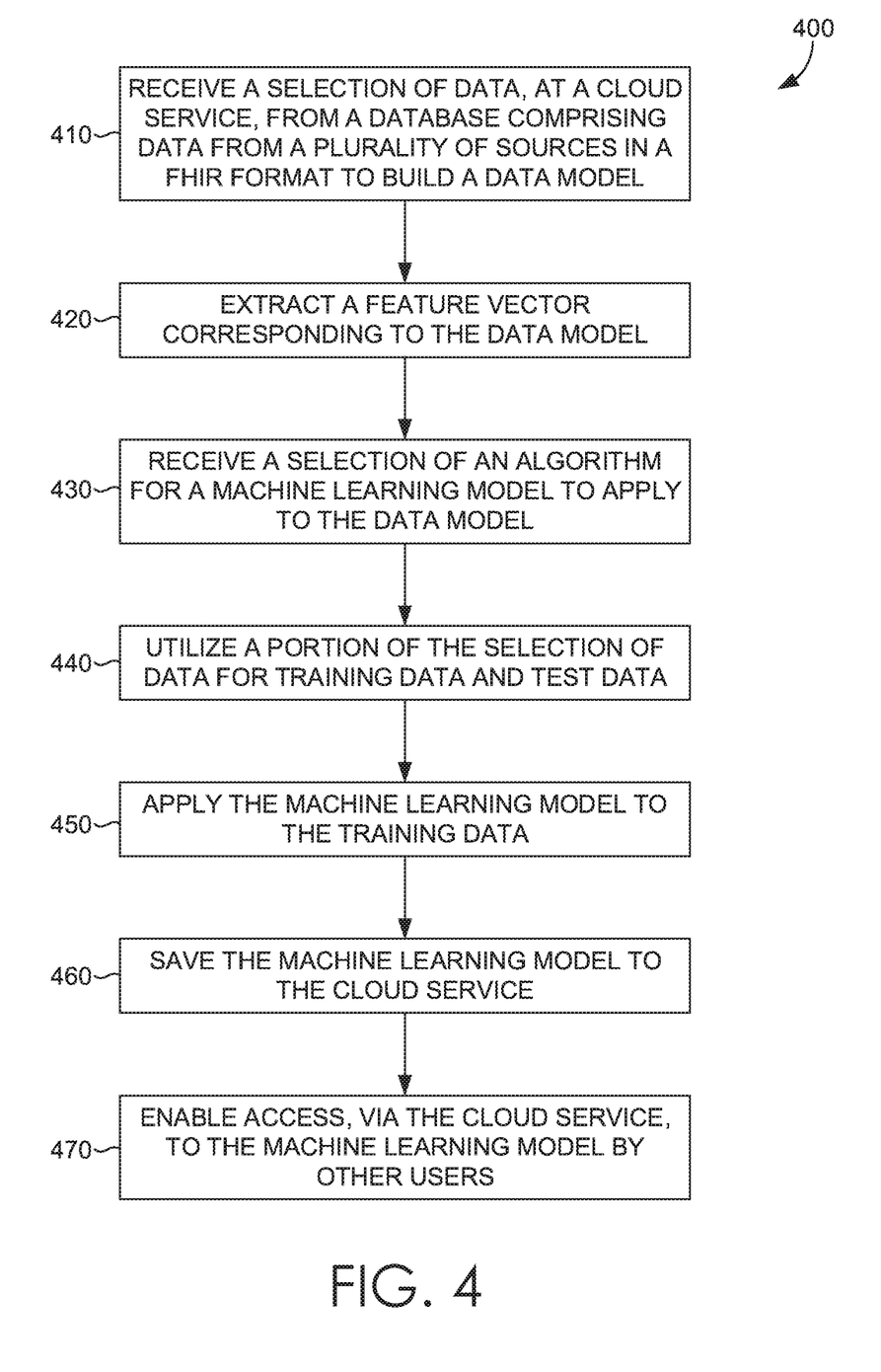
FIG. 4 is a flow diagram of an exemplary method of providing closed-loop intelligence in accordance with an embodiment of the present invention.

Turning now to FIG. 4, a flow diagram is depicted of an exemplary method 400 of providing closed-loop intelligence, in accordance with an embodiment of the present disclosure. For instance, the method 400 may be employed utilizing the closed-loop intelligence system 200, 300 of FIGS. 2 and 3, respectively. As shown at step 410, a selection of data is received, at a cloud service, from a database comprising data from a plurality of sources in a Fast Healthcare Interoperability Resources (FHIR) format to build a data model. For example, a user may issue a query, such as the example in Table 1, to select all data from a particular table in a database.

TABLE 1 spark.sql("select * from example_timeseries").limit(10).toPandas( )

In response the data from the particular table in the database is returned, as illustrated in Table 2.

TABLE 2

| | patient_id | year | month | birthDate | avg_glucose_level | avg_bun |
|---|---|---|---|---|---|---|
| 0 | urn:cerner:empi:00226841-584d-4454-a896-0bd68a... | 2010 | 7 | 1944 Jan. 1 | 105.00000000 | 14.00000000 |
| 1 | urn:cerner:empi:00226841-584d-4454-a896-0bd68a... | 2010 | 7 | 1944 Jan. 1 | 105.00000000 | 14.00000000 |
| 2 | urn:cerner:empi:00226841-584d-4454-a896-0bd68a... | 2010 | 7 | None | 105.00000000 | 14.00000000 |
| 3 | urn:cerner:empi:009b4a86-6084-4d96-8059-f42a92... | 2010 | 6 | None | None | None |
| 4 | urn:cerner:empi:009b4a86-6084-4d96-8059-f42a92... | 2010 | 6 | 1985 Jan. 1 | None | None |
| 5 | urn:cerner:empi:009b4a86-6084-4d96-8059-f42a92... | 2010 | 6 | 1985 Jan. 1 | None | None |
| 6 | urn:cerner:empi:016d1d75-b8f4-43be-8649-2969a7... | 2010 | 6 | None | None | None |
| 7 | urn:cerner:empi:016d1d75-b8f4-43be-8649-2969a7... | 2010 | 6 | 1924 Jan. 1 | None | None |
| 8 | urn:cerner:empi:016d1d75-b8f4-43be-8649-2969a7... | 2010 | 6 | 1924 Jan. 1 | None | None |
| 9 | urn:cerner:empi:01713a3b-100d-4de9-86f2-d70c81... | 2010 | 11 | 1992 Jan. 1 | None | None |

| | patient_id | avg_creatinine | avg_sodium | hypertension | chest_pain | heart_failure |
|---|---|---|---|---|---|---|
| 0 | urn:cerner:empi:00226841-584d-4454-a896-0bd68a... | 1.20000000 | 137.00000000 | True | False | False |
| 1 | urn:cerner:empi:00226841-584d-4454-a896-0bd68a... | 1.20000000 | 137.00000000 | True | False | False |
| 2 | urn:cerner:empi:00226841-584d-4454-a896-0bd68a... | 1.20000000 | 137.00000000 | True | False | False |
| 3 | urn:cerner:empi:009b4a86-6084-4d96-8059-f42a92... | None | None | False | False | False |
| 4 | urn:cerner:empi:009b4a86-6084-4d96-8059-f42a92... | None | None | False | False | False |
| 5 | urn:cerner:empi:009b4a86-6084-4d96-8059-f42a92... | None | None | False | False | False |
| 6 | urn:cerner:empi:016d1d75-b8f4-43be-8649-2969a7... | None | None | False | False | False |
| 7 | urn:cerner:empi:016d1d75-b8f4- | None | None | False | False | False |

TABLE 2-continued

|   | | | | | | |
|---|---|---|---|---|---|---|
| 8 | urn:cerner:empi:0 16d1d75-b8f4- 43be-8649- 2969a7... | None | None | False | False | False |
| 9 | urn:cerner:empi:0 1713a3b-100d- 4de9-86f2- d70c81... | None | None | False | False | False |

In some embodiments, SQL transformations may be initially performed on the data, such as by issuing the command in Table 3.

TABLE 3

```
from pyspark.ml.feature import SQLTransformer
to_numeric = SQLTransformer(statement="""
select avg_glucose_level,
    avg_bun,
    avg_creatinine,
    if(hypertension,1,0) hypertension,
    if(chest_pain,1,0) chest_pain,
    if(heart_failure,1,0) heart_failure
from _THIS_
where avg_glucose_level is not null and
    avg_bun is not null and
    avg_creatinine is not null
""")
```

Specific features may be considered, such as by issuing the command illustrated in Table 4.

TABLE 4

```
from pyspark.ml.feature import SQLTransformer
to_numeric = SQLTransformer(statement="""
select avg_glucose_level,
    avg_bun,
    avg_creatinine,
    if(hypertension, 1,0) hypertension,
    if(chest_pain,1,0) chest_pain,
    if(heart_failure,1,0) heart_failure
from _THIS_
where avg_glucose_level is not null and
    avg_bun is not null and
    avg_creatinine is not null
""")
```

At step 420, a feature vector corresponding to the data model is extracted. For example, a user may issue the command illustrated in Table 5, a feature vector can be extracted from the inputs "average glucose level," average creatinine," and "chest pain."

TABLE 5

```
from pyspark.ml.feature import Vector Assembler
# Assemble columns into a feature vector
assemble_features = Vector Assembler(
    inputCols=['avg_glucose_level', 'avg_creatinine','chest_pain'],
    outputCol="features")
```

A selection of an algorithm is received, at step 430, for a machine learning model to apply to the data model. For example, a user may issue a command illustrated in Table 6, to utilize logistic regression to predict heart failure based on the features extracted in Table 5.

TABLE 6

```
from pyspark.ml.classification import LogisticRegression
from pyspark.ml import Pipeline
# Predict the heart failures based on the above features,
regression = LogisticRegression(featuresCol='features',
                    labelCol= 'heart_failure',
                    maxIter=10)
# Build the pipeline
pipeline = Pipeline(stages=[to_numeric,
                    assemble_features,
                    regression])
```

At step 440, a portion of the selection of data is utilized for training data and test data. For example, the time series data can be split into training and testing data and the model can be applied by issuing the command illustrated in Table 7.

TABLE 7

```
(train,test) = spark.sql('select * from example_timeseries').randomSplit
([0.6, 0.4])
model = pipeline.fit(train)
scored = model.transform(test)
scored.cache( )
scored.limit(5).toPandas()
```

The machine learning model is applied, at step 450, to the training data. An exemplary output of the model is illustrated in Table 8.

TABLE 8

| | avg_glucose level | avg_ bun | avg_ creatinine | hypertension | chest_ pain |
|---|---|---|---|---|---|
| 0 | 105.0000000 | 14.00000000 | 1.20000000 | 1 | 0 |
| 1 | 88.00000000 | 17.00000000 | 1.20000000 | 0 | 0 |
| 2 | 88.00000000 | 17.00000000 | 1.20000000 | 0 | 0 |
| 3 | 88.00000000 | 17.00000000 | 1.20000000 | 0 | 0 |
| 4 | 89.00000000 | 13.00000000 | 1.50000000 | 1 | 0 |

| | heart_ failure | features | rawPrediction | probability | prediction |
|---|---|---|---|---|---|
| 0 | 0 | [105.0, 1.2, 0.0] | [3.18752542382, 3.18752542382] | [0.960362128712, 0.0396378712883] | 0.0 |

TABLE 8-continued

| | | | | | |
|---|---|---|---|---|---|
| 1 | 0 | [88.0, 1-2, 0.0] | [3.2383841835, 3.2383841835] | [0.962253464049, 0.0377465359511] | 0.0 |
| 2 | 0 | [88.0, 1-2, 0.0] | [3.2383841835, 3.2383841835] | [0.962253464049, 0.0377465359511] | 0.0 |
| 3 | 0 | [88.0, 1-2, 0.0] | [3.2383841835, 3.2383841835] | [0.962253464049, 0.0377465359511] | 0.0 |
| 4 | 0 | [89.0, 1.5, 0.0] | [3.2063350953, 3.2063350953] | [0.961071983285, 0.0389280167153] | 0.0 |

A classifier may be assigned based on the output of the model. For example, the command illustrated in Table 9 may be issued, resulting in the classification illustrated in Table 10.

TABLE 9

```
from pyspark.ml.evaluation import BinaryClassificationEvaluator
evaluator = BinaryClassificationEvaluator(rawPredictionCol=
"rawPrediction",
                  labelCol="heart_failure",
                  metricName= "areaUnderROC")
evaluator.evaluate(scored)
```

TABLE 10

0.6710423781237312

As can be appreciated, a trained model results. At step 460, the machine learning model is saved, including any SQL transformations and feature vector extraction, to the cloud service. Access is enabled, at step 470, via the cloud service, to the machine learning model by other users. This enables other systems to load and run the model to perform predictions against real data. In various embodiments, the number of processors utilized to train and test the machine learning model is dynamic.

Figure 5:
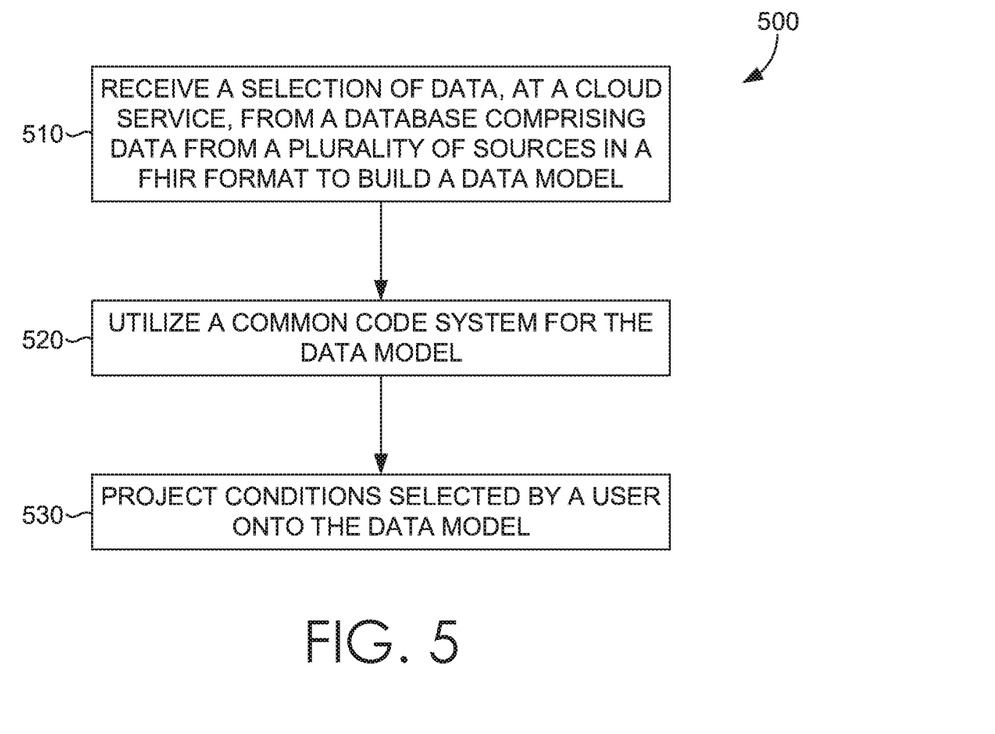
FIG. 5 is a flow diagram of an exemplary method of providing closed-loop intelligence in accordance with an embodiment of the present invention.

Turning now to FIG. 5, a flow diagram is depicted illustrating an exemplary method 500 of providing closed-loop intelligence, in accordance with an embodiment of the present disclosure. For instance, the method 500 may be employed utilizing a cloud service, such as the closed-loop intelligence system 200, 300 of FIGS. 2 and 3, respectively. As shown at step 510, a selection of data is received at a cloud service. The selection of data is made from a database comprising data from a plurality of sources in a FHIR format and is used to build a data model. Typically, one logical database is utilized per populations, and other databases may be used for other needs. Each logical database corresponds to groups of tables that can be queried by anyone with appropriate authorization. An exemplary data model is illustrated in Table 11.

TABLE 11

| | database | tableName | isTemporary |
|---|---|---|---|
| 0 | fhir_example | allergyintolerances | False |
| 1 | fhir_example | conditions | False |
| 2 | fhir_example | encounters | False |
| 3 | fhir_example | medicationstatements | False |
| 4 | fhir_example | observations | False |
| 5 | fhir_example | patients | False |
| 6 | fhir_example | procedures | False |

A user may select the table "conditions" from the data model. At step 520, a common code system, such as one defined by the Value Set Authority Center (VSAC) is utilized for the data model. For example, the user may issue a command to utilize the common code system for the data model, such as the command shown in Table 12.

TABLE 12

| push_valuesets(spark, | |
|---|---|
| {'body_weight' | : isa_loinc('29463-7'), |
| 'bmi' | : isa_loinc('39156-5'), |
| 'asthma' | : isa_snomed('195967001'), |
| 'stroke' | : isa_snomed('230690007'), |
| 'hypertension' | : isa_snomed('59621000'), |
| 'diabetes' | : isa_snomed('313436004'), |
| 'afib' | : isa_snomed('49436004'), |
| 'copd' | : isa_snomed('42343007'), |
| 'chest_pain' | : isa_snomed('29857009'), |
| 'anemia' | : isa_snomed('271737000'), |
| 'ckd' | : isa_snomed('433144002'), |
| 'apnea' | : isa_snomed('78275009'), |
| 'cardiac_arrythmia' | : isa_snomed('49436004'), |
| 'heart_failure' | : isa_snomed('42343007'), |
| 'esrd' | : isa_snomed('46177005'), |
| 'serum_creatinine' | : isa_loinc('2160-0'), |
| 'bun' | : isa_loinc('3094-0'), |
| 'glucose_level' | : isa_loinc('2345-7'), |
| 'serum_potassium' | : isa_loinc('2823-3'), |
| 'serum_sodium' | : isa_loinc('2951-2')}) |

At step 530, conditions selected by a user are projected onto the data model. For example, the user may issue a command to project conditions onto the data model, such as the command illustrated in Table 13.

TABLE 13

```
glucose_levels = spark.sql("""
select subject.reference,
    code.coding[0].code code,
    valueQuantity.value,
    effectiveDateTime
from observations
where in_valueset(code, 'glucose_level') and
    valueQuantity.value is not null
""")
glucose_levels.limit(10).toPandas( )
```

In response, the cloud service may return the data model having data that includes only the requested conditions or valueset. For example, the data model illustrated in Table 14 may be returned.

TABLE 14

| reference | code | value | effectiveDateTime |
|---|---|---|---|
| 0 urn:cerner:empi:a7943425-2420-4403-9fcf-0fae4e... | 2345-7 | 91.0000 | 2010-11-26T16:00:00Z |
| 1 urn:cerner:empi:30ced248-c37d-485f-92ee-184a09... | 2345-7 | 101.0000 | 2010-11-29T06:00:00Z |
| 2 urn:cerner:empi:91a843a8-9be1-41df-87df-fae86d... | 2345-7 | 89.0000 | 2010-09-13T06:00:00Z |
| 3 urn:cerner:empi:1cacfba5-647b-425c-bdd3-70b32a... | 2345-7 | 84.0000 | 2010-04-05T06:00:00Z |
| 4 urn:cerner:empi:91a31172-5557-47ff-936d-63020e... | 2345-7 | 72.0000 | 2010-04-08T16:35:00Z |
| 5 urn:cerner:empi:98ad8355-239b-4ce3-b41f-d5baf2... | 2345-7 | 108.0000 | 2010-11-24T06:00:00Z |
| 6 urn:cerner:empi:edae1c7b-5fb3-4e81-8570-4ff335... | 2345-7 | 82.0000 | 2010-08-13T19:00:00Z |
| 7 urn:cerner:empi:98ad8355-239b-4ce3-b41f-d5baf2... | 2345-7 | 178.0000 | 2010-07-27T06:00:00Z |
| 8 urn:cerner:empi:a00f8d5e-942e-4445-bf4c-c6e0ad... | 2345-7 | 68.0000 | 2010-01-04T20:00:00Z |
| 9 urn:cerner:empi:1ada9444-3f01-45a8-9767-dda8a9... | 2345-7 | 88.0000 | 2010-04-28T06:00:00Z |

In addition to creating graphs using the data model, in some embodiments, the data model can be converted into a time series structure. For example, the user may issue a command to convert the data model into a time series structure, such as the command illustrated in Table 15.

TABLE 15

```
conditions = spark.sql("""
select subject.reference patient_id,
    year(onsetDateTime) year,
    month(onsetDateTime) month,
    max(if(in_valueset(code, 'hypertension'),
       true,
       false)) hypertension,
    max(if(in_valueset(code, 'chest_pain'),
       true,
       false)) chest_pain,
    max(if(in_valueset(code, 'heart_failure'),
       true,
       false)) heart_failure
from conditions
where onsetDateTime < '2011-01-01' and
    onsetDateTime >= '2010-01-01'
group by subject.reference,
    year(onsetDateTime),
    month(onsetDateTime)
order by patient_id, year, month
""").cache( )
```

In response, a time series structure, such as the time series structure illustrated in Table 16 may be returned.

TABLE 16

| | patient id | year | month | hypertension | chest pain | heart failure |
|---|---|---|---|---|---|---|
| 0 | urn:cerner:empi:0001180a-dbe7-48e4-a8f7-a1fe46... | 2010 | 2 | False | False | False |
| 1 | urn:cerner:empi:0001180a-dbe7-48e4-a8f7-a1fe46... | 2010 | 11 | False | False | False |
| 2 | urn:cerner:empi:0001ba40-0401-4c76-8571-23151e... | 2010 | 1 | True | False | False |
| 3 | urn:cerner:empi:0001ba40-0401-4c76-8571-23151e... | 2010 | 4 | True | False | False |
| 4 | urn:cerner:empi:0001ba40-0401-4c76-8571-23151e... | 2010 | 7 | False | False | False |
| 5 | urn:cerner:empi:0001ba40-0401-4c76-8571-23151e... | 2010 | 8 | True | False | False |
| 6 | urn:cerner:empi:0001ba40-0401-4c76-8571-23151e... | 2010 | 9 | True | False | False |
| 7 | urn:cerner:empi:0001ba40-0401-4c76-8571-23151e... | 2010 | 10 | True | False | False |
| 8 | urn:cerner:empi:0001ba40-0401-4c76-8571-23151e... | 2010 | 11 | False | False | False |
| 9 | urn:cerner:empi:0001ba40-0401-4c76-8571-23151e... | 2010 | 12 | False | False | False |

In some embodiments, the data model and/or the time series structure can be saved at the cloud service. Additionally, access to the data model and or the time series structure by other users may be enabled via the cloud service. In some embodiments, a number of processors utilized by components of the cloud service to build the data model and/or the time series structure is dynamic.

As can be understood, embodiments of the present disclosure provide for an objective approach for providing closed-loop intelligence. The present disclosure has been described in relation to particular embodiments, which are intended in all respects to be illustrative rather than restrictive. Alternative embodiments will become apparent to those of ordinary skill in the art to which the present disclosure pertains without departing from its scope.

From the foregoing, it will be seen that this disclosure is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. One or more non-transitory computer-storage media storing computer-useable instructions that, when used by one or more processors, cause the one or more processors to perform operations comprising:
   receiving a selection of data, at a cloud service, from a database comprising data from a plurality of sources in a Fast Healthcare Interoperability Resources (FHIR) format to build a data model, wherein the data comprises internal data of a particular healthcare organization and external data from other healthcare organizations;
   extracting a feature vector corresponding to the data model;
   receiving a selection of an algorithm for a machine learning model to apply to the data model;
   utilizing a portion of the selection of data for training data and test data;
   applying the machine learning model to the training data;
   enabling the other healthcare organizations to access and utilize the trained machine learning model and the data comprising internal data of a particular healthcare organization and external data from other healthcare organizations; and
   pushing insights gained from the trained machine learning model based on the data comprising internal data of a particular healthcare organization and external data from other healthcare organizations into a clinical workflow.

2. The media of claim 1, further comprising saving the trained machine learning model at the cloud service.

3. The media of claim 2, further comprising enabling access, via the cloud service, to the trained machine learning model by other users.

4. The media of claim 1, further comprising enabling access, via the cloud service, to the selection of data by other users.

5. The media of claim 1, wherein a number of processors utilized to train the machine learning model is dynamic.

6. The media of claim 1, wherein a number of processors utilized to test the machine learning model is dynamic.

7. A system in a healthcare computing environment comprising:
   a processor; and
   a non-transitory computer storage medium storing computer-useable instructions that, when used by the processor, causes the processor to:
   receiving a selection of data, at a cloud service, from a database comprising data from a plurality of sources in a Fast Healthcare Interoperability Resources (FHIR) format to build a data model, wherein the data comprises internal data of a particular healthcare organization and external data from other healthcare organizations;
   extracting a feature vector corresponding to the data model;
   receive a selection of an algorithm for a machine learning model to apply to the data model;
   utilizing a portion of the selection of data for training data and test data;
   applying the machine learning model to the training data;
   enabling the other healthcare organizations to access and utilize the trained machine learning model and the data comprising internal data of a particular healthcare organization and external data from other healthcare organizations; and
   pushing insights gained from the trained machine learning model based on the data comprising internal data of a particular healthcare organization and external data from other healthcare organizations into a clinical workflow.

8. The system of claim 7, further comprising saving the trained machine learning model at the cloud service.

9. The system of claim 7, further comprising receiving content for a data model, the content being received automatically from a plurality of healthcare systems.

10. The system of claim 9, further comprising assembling the content into FHIR views.

11. The system of claim 7, further comprising enabling the content to be utilized for analytics and machine learning.

12. The system of claim 9, wherein the plurality of healthcare systems comprise electronic medical records, personal health records, care management systems, or third party content.

13. The system of claim 10, wherein assembling the content into FHIR views comprises normalizing the content.

14. A computerized method comprising:
   receiving a selection of data, at a cloud service, from a database comprising data from a plurality of sources in a Fast Healthcare Interoperability Resources (FHIR) format to build a data model, wherein the data comprises internal data of a particular healthcare organization and external data from other healthcare organizations;
   extracting a feature vector corresponding to the data model;
   receive a selection of an algorithm for a machine learning model to apply to the data model;
   utilizing a portion of the selection of data for training data and test data;
   applying the machine learning model to the training data;
   enabling the other healthcare organizations to access and utilize the trained machine learning model and the data comprising internal data of a particular healthcare organization and external data from other healthcare organizations; and
   pushing insights gained from the trained machine learning model based on the data comprising internal data of a particular healthcare organization and external data from other healthcare organizations into a clinical workflow.

15. The method of claim 14, further comprising saving the trained machine learning model at the cloud service.

16. The method of claim 14, further comprising receiving content for a data model, the content being received automatically from a plurality of healthcare systems.

17. The method of claim 16, further comprising assembling the content into FHIR views.

18. The method of claim 14, further comprising enabling the content to be utilized for analytics and machine learning.

19. The method of claim 16, wherein the plurality of healthcare systems comprise electronic medical records, personal health records, care management systems, or third party content.

20. The method of claim 17, wherein assembling the content into FHIR views comprises cleaning and normalizing the content.

* * * * *